United States Patent
Rabben et al.

(10) Patent No.: US 8,224,053 B2
(45) Date of Patent: Jul. 17, 2012

(54) METHODS AND SYSTEMS FOR DISPLAYING QUANTITATIVE SEGMENTAL DATA IN 4D RENDERING

(75) Inventors: Stein Rabben, Sofiemyr (NO); Stian Langeland, Vestfold (NO)

(73) Assignee: General Electric Company, Schenectady, NY (US)

( * ) Notice: Subject to any disclaimer, the term of this patent is extended or adjusted under 35 U.S.C. 154(b) by 523 days.

(21) Appl. No.: 12/414,928

(22) Filed: Mar. 31, 2009

(65) Prior Publication Data

US 2010/0246911 A1 Sep. 30, 2010

(51) Int. Cl.
*G06K 9/00* (2006.01)
(52) U.S. Cl. ...................................................... 382/131
(58) Field of Classification Search .................. None
See application file for complete search history.

(56) References Cited

U.S. PATENT DOCUMENTS

| | | | |
|---|---|---|---|
| 2005/0228276 A1 | 10/2005 | He et al. | |
| 2005/0232489 A1 | 10/2005 | Hosoda et al. | |
| 2006/0004291 A1 | 1/2006 | Heimdal et al. | |
| 2010/0183074 A1* | 7/2010 | Furukawa et al. | ....... 375/240.16 |

FOREIGN PATENT DOCUMENTS

WO  WO 2009/011442  * 7/2008

* cited by examiner

*Primary Examiner* — Tu Nguyen
(74) *Attorney, Agent, or Firm* — The Small Patent Law Group; Dean D. Small (57) ABSTRACT

A method and system for displaying quantitative segmental data in a 4D presentation along with local deformation is disclosed herewith. The method comprises: identifying a segment in a volumetric image data. Then, the following steps are iterated to produce a four-dimensional rendering. The iterated steps include: tracking the segment of the volumetric image data to produce a displacement field. Local deformation of the segment is identified using the displacement field. And the segment is rendered with reference to the displacement field and the local deformation.

22 Claims, 9 Drawing Sheets

METHODS AND SYSTEMS FOR DISPLAYING QUANTITATIVE SEGMENTAL DATA IN 4D RENDERING

FIELD OF INVENTION

This invention relates generally to methods and systems for presenting of segmental quantitative measurements in a four-dimensional (4D) rendering. The methods and systems are particularly useful in medical imaging.

BACKGROUND OF INVENTION

New medical imaging technology permits regional quantitative 4D analysis of objects, such as the myocardium of a patient's heart. The regional quantitative 4D analysis provides detailed information on the motion and deformation of all material points in the object. However, while analyzing the data, it is beneficial to divide the data into different segments. For example, in cardiology, it is common to divide the cardiac structure into segments.

Additionally, because of tethering effects, it is often difficult to distinguish motion caused by deforming neighbor segments from motion caused by the segments own deformation, thereby making it difficult for an operator to distinguish local deformation from the overall motion of each segment.

Thus, it will be beneficial to provide a method and system for enhancing the visual perception of segmental deformation by displaying each segment on its own.

BRIEF DESCRIPTION OF INVENTION

In one aspect, some embodiments of the present invention provide a method of displaying quantitative segmental data in a 4D presentation of an object. The method comprises: identifying a segment in a volumetric image data. Then the following steps are iterated to display a segmental rendering with local deformation. The iterated steps include: tracking the segment of the volumetric image data to produce a displacement field; identifying local deformation of the segment based on the displacement field; and rendering the segment with reference to the displacement field and the local deformation.

In another aspect, some embodiments of the present invention provide a method of improving visual perception of cardiac segmental deformation display in a three-dimensional rendering. The method comprises: obtaining a volumetric cardiac image and defining at least one segment on the cardiac image based on a reference. Then, the following steps are iterated to improve visual perception of cardiac segmental deformation display. The iterated steps include: estimating a displacement field by tracking the segment to identify the motion of the segment; identifying local deformation of the segment from the displacement field; and rendering the segment with reference to the displacement field and mapping the local deformation onto the rendering.

In another aspect, some embodiments of the present invention provide a system that includes: a computer or processor, memory, and a display. The system is configured to identify a segment of an object in volumetric image data. The system further comprises: a tracking module configured to track the segment to produce a displacement field; an analysis module configured to identify local deformation of the segment from the displacement field; and a rendering module configured to render the segment with reference to the displacement field; wherein the tracking module, analysis module and rendering module are configured to operate iteratively to thereby produce a visually enhanced segmental deformation display in a 4D presentation.

In yet another aspect, some embodiments of the present invention provide a machine-readable medium or media having recorded thereon instructions configured to instruct an system that comprises a computer or processor, memory, and a display. The media comprises: a routine for obtaining displacement field representing motion of a segment; a routine for identifying local deformation of the segment from the displacement field; and a routine for rendering the segment with reference to the displacement field thereby displaying the local deformation.

DETAILED DESCRIPTION OF INVENTION

The foregoing summary, as well as the following detailed description of certain embodiments of the present invention, will be better understood when read in conjunction with the appended drawings. To the extent that the figures illustrate diagrams of functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property. Moreover, the terms "computer" and "processor" are used interchangeably herein to refer to either specialized hardware to perform digital signal processing, control, data manipulation, and/or calculations, or a general purpose computer that can be programmed to perform the same functions and/or adapted to interface with external digital signals. The phrases "computer or processor" and "processor or computer" are therefore intended to have equal scope with either of the individual terms and are not intended to imply a dichotomy between the two terms.

Technical effects of embodiments of the present invention include providing an improved method of displaying quantitative segmental data in 4D representation. Some embodiments of the present invention include identifying local deformation of a segment and displaying the same with a relevant segment. Furthermore, some embodiments of the present invention facilitate using color coding to represent the quantitative regional parameters. The segment surfaces may also be textured to generate a realistic display of segment deformation. Also, in some embodiments, quantitative regional parameters are identified and superimposed on the texture as color codes. Thus, segment rendering superimposed with a color-coded texture, representing quantitative regional parameters and local deformation, provides an enhanced display of segment deformation.

Figure 1:
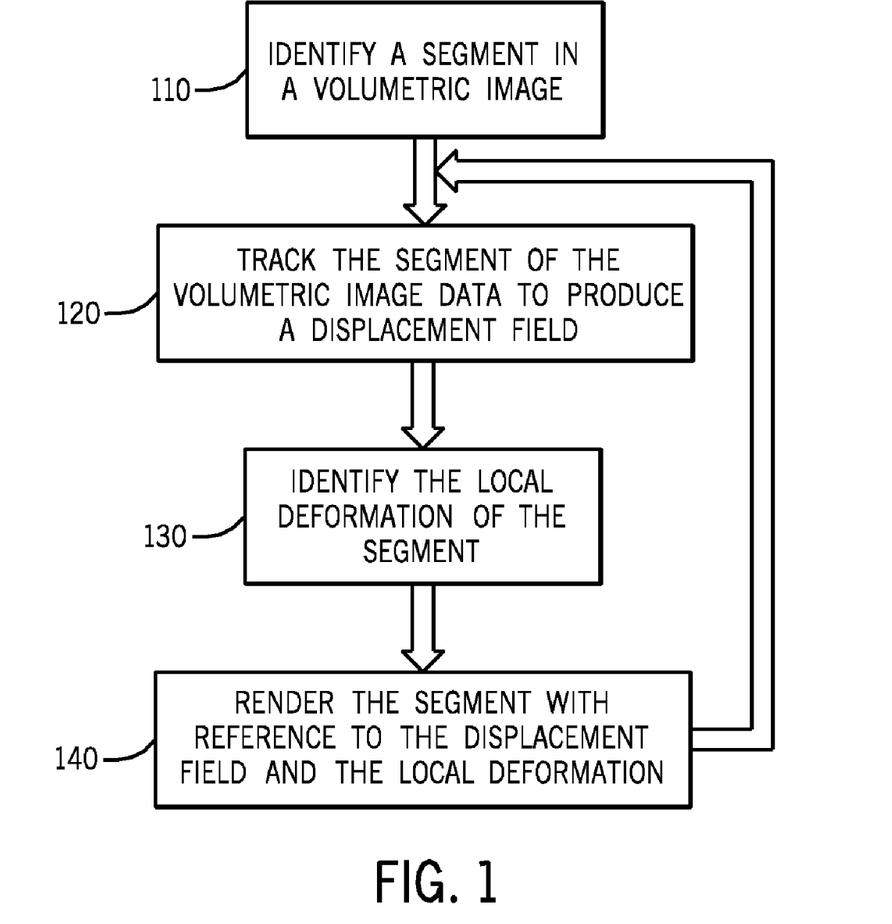
FIG. 1 is a flowchart illustrating a method of visually enhancing display of segmental motion in a 4D presentation of an object as described in an embodiment of the invention.

FIG. 1 is a flowchart illustrating a method of visually enhancing display of segmental motion in a 4D presentation of an object as described in an embodiment of the invention. At step 110, a segment is identified in a volumetric image at a point in time. The segment is defined at a particular reference time, such as end-diastole. The segment definition can be arbitrarily chosen, for example, at a coronary territory or based on standard 16, 17 or 18 segment models commonly used in cardiology. Then, in the remaining frames of the cardiac cycle, the initial segment is displaced based on the tracking results. In an example, the volumetric image may be a sequence of volumetric images of a moving object, such as a moving organ. The term volumetric image or volumetric image data conveys a volumetric image sequence representing motion of the object. The volumetric image can be obtained using ultrasound imaging, magnetic resonance imaging, 3D or 4D computed tomographic imaging, or any other imaging technique. The segment from a volumetric image may be identified by using various algorithms or devices used in the industry. A region of interest may be defined in the volumetric image and the region of interest may be defined as different segments. A clinician can select the region of interest based on various requirements and define the segments. However, the segments can also be identified manually or automatically. Once the segment is identified, the following steps 120 to 140 can be repeated for available time steps in the volumetric image sequence. At step 120, the segment is tracked to produce a displacement field. The displacement field represents the overall motion of the selected segment. A suitable tracking technique may be used to estimate the displacement field. At step 130, local deformation of the segment is estimated from the displacement field. The local deformation of the segment is defined by the local variation in displacement field regardless of the overall motion of neighboring segments. In an embodiment, the local deformation of a segment is calculated from the overall motion of the segment. The overall motion of the segment represent the motion of the segment caused by its local deformation along with the motion caused by adjacent or other segments defined in the cardiac image or in the selected region of interest. The overall motion of the segment is subtracted from the average motion of the segment obtained by averaging the motion of all the points in the segment. This gives the local deformation of the segment. However any tracking or image processing algorithm may be used to identify the local deformation of the segment. At step 140, the segment is rendered with reference to the displacement and the local deformation of the segment. The rendering may be surface rendering or volume rendering. The surface or volume rendering of the segment with reference to the displacement field and local deformation may be achieved by known rendering methods. The rendering is done based on the displacement field and local deformation is mapped onto the rendering.

In an embodiment, the segment is surface rendered with reference to the displacement field, displaying the local deformation of the segment. In an embodiment, the surface rendering of the segment may be generated using wire frame models, artificial textured models, or semi-transparent models. Further, in an embodiment, static wire frame models or static semi-transparent models from a reference time can be displayed together with the dynamic surface model of the segment.

In an embodiment, the segment is volume rendered with reference to the displacement field, displaying the local deformation of the segment. In an example, the volume rendering may be generated by using dynamic cropping surfaces as segment boundaries. In another example, the volume renderings may be generated from synthetically generated still frame 3D data, e.g., from data with an artificial speckle pattern, where the data is moved according to the results of the 3D tracking. Alternately, the volume rendering may be generated from still frame 3D data from other imaging modalities such as Magnetic Resonance Imaging (MRI) and 3-dimensional Computer Tomography (CT).

In an embodiment, at least one quantitative regional parameter may be identified while tracking the segment. Some examples of the quantitative regional parameters include velocity, strain, displacement, etc. The quantitative regional parameters may vary based on the displacement of the segment. For example, in a cardiac image, strain in the cardiac walls during different stages of a cardiac cycle will be different. The quantitative regional parameters may be estimated at different stages and may be represented as color codes or deformation markers, so that these quantitative regional parameters can be easily visualized. Thus, in some of the embodiments, the quantitative regional parameters are represented as color codes or deformation markers, and they may be superimposed onto a texture or to the surface or to a volume rendering. It is to be noted that the color codes may be superimposed onto the texture. Thus, the workflow generates a 4D surface rendered image with texture having color codes representing at least one quantitative regional parameter, thereby enhancing local deformation of the segment.

In an embodiment, different textures, such as texture in the form of a speckle pattern, texture looking like organ tissue, and texture based on renderings from any imaging modality, may be used. The imaging modality could include any imaging modality and need not be limited to the modality by which the initial the volumetric images were acquired.

In an embodiment, a plurality of segment may be displayed adjacently in a display at the same time. Visual comparison of the segment deformation is facilitated thereby.

Figure 2:
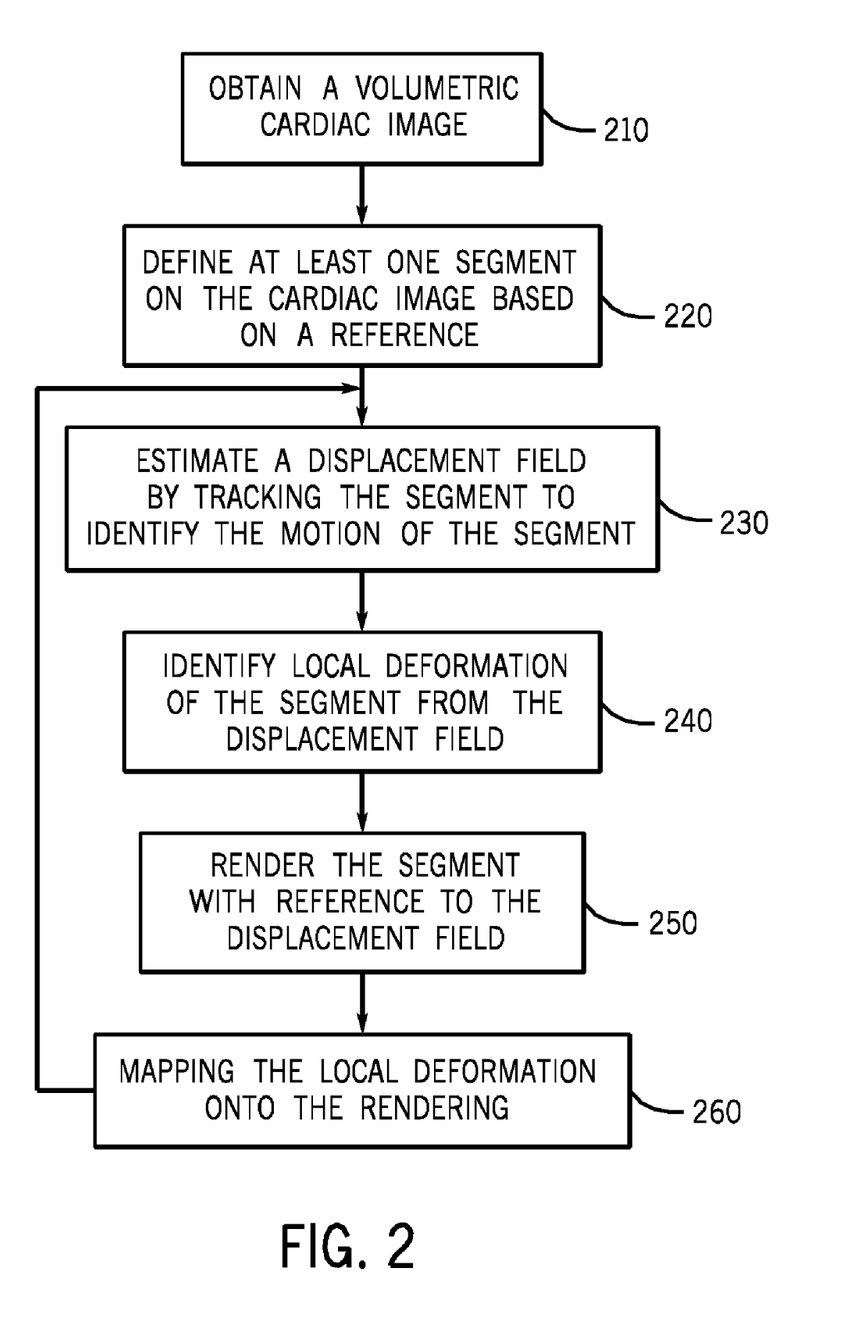
FIG. 2 is a flowchart illustrating a method of enhancing display of a cardiac segmental motion in a surface or volume rendering as described in an embodiment of the invention.

FIG. 2 is a flowchart illustrating a method of enhancing display of cardiac segmental motion in a 3D rendering as described in an embodiment of the invention. At step 210, a volumetric cardiac image is obtained. The image may be obtained using any imaging system. In an example, the image is a cardiac ultrasound volumetric image. At step 220, a cardiac segment is defined for a reference time. At step 230, the segment is tracked for obtaining a displacement field representing the motion of the segment. The displacement field can be estimated using a suitable tracking method. At step 240, local deformation of the segment is obtained. In an embodiment, the local deformation of a segment is obtained from the displacement field of the segment. The displacement field of the segment represents motion caused by adjacent tissue along with the local displacement of the segment caused by its local deformation. Local deformation could be obtained by any known analysis method. At step 250, the segment is rendered with reference to the displacement field. The segment could be volume or surface rendered. At step 260, the identified local deformation is mapped into the rendering and displayed. This will result in a visually enhanced segmental deformation display in a 4D presentation.

The rendering could be surface rendering or volume rendering.

In an embodiment, by tracking the region of interest, at least one quantitative regional parameter, such as strain, velocity, displacement, etc, in the segment due to motion may be identified. The quantitative regional parameters are obtained from the displacement field and presented as color codes in the renderings. This will enhance the display.

In an embodiment, the enhanced display could be achieved by using images from more than one imaging system. The method for combined 4D presentation of quantitative segmental data of an object could include receiving a static segment from a volumetric image of an object, which could be obtained by a template imaging system. Once the segment is defined, the segment may be aligned with reference to volumetric images obtained from a first imaging system. In the volumetric image obtained by the first imaging system, a segment similar to the one identified with reference to the template imaging system is defined. The displacement field corresponding to the motion of the segment defined in the volumetric images acquired by the first imaging system is obtained. The segment defined by the template imaging system is rendered with reference to the displacement field identified by the first imaging system. From the displacement field identified, the local deformation of the segment may be obtained and the rendered segment may be displaced with the local deformation. In an embodiment, the template and first imaging system includes an ultrasound imaging system, magnetic resonance imaging system, and/or computed tomographic imaging system.

Figure 3:
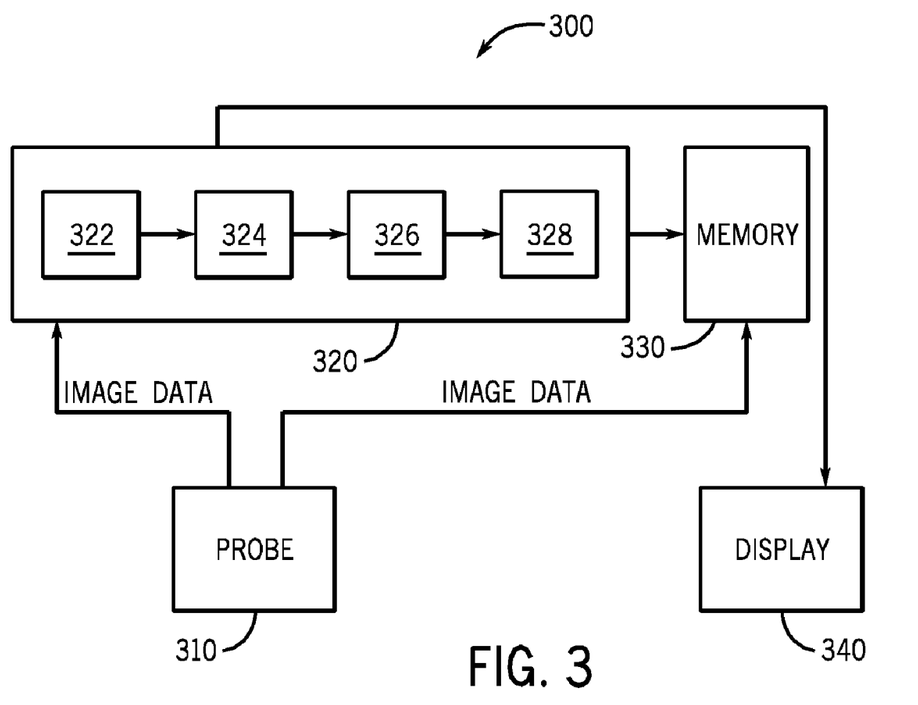
FIG. 3 is block diagram of a system capable of displaying visually enhanced display of motion in a 4D presentation of an object as described in an embodiment of the invention.

FIG. 3 is a block diagram of a system 300 capable of displaying visually enhanced display of motion in a 4D presentation of an object as described in an embodiment of the invention. The system 300 is configured to have a probe or transducer 310 configured to acquire raw medical image data. The system 300 may acquire volumetric images of a moving object and store it in an image-storing device. In some embodiments, the probe 310 is an ultrasound transducer and the system 300 is an ultrasound imaging system. A memory 330 stores acquired raw image data, which may be processed by a processor 320 in some embodiments of the present invention. A display 340 (e.g., an internal display) is also provided and configured to display a medical image in various forms, such as surface renderings or volume renderings.

To display a medical image obtained using the probe 310, the processor 320 is provided with a software or firmware memory 322 containing instructions to perform image-processing techniques on the acquired raw medical image data. Although shown separately in FIG. 3, it is not required that the software memory 322 and memory 330 be physically separate memories. Dedicated hardware may be used instead of software and/or firmware for performing image processing, or a combination of dedicated hardware and software, or software in combination with a general purpose processor, or a digital signal processor. Once the requirements for such software and/or hardware and/or dedicated hardware are gained from an understanding of the descriptions of embodiments of the invention contained herein, the choice of any particular implementation may be left to a hardware engineer and/or software engineer. However, any dedicated and/or special purpose hardware or special purpose processor is considered subsumed in the block labeled processor 320.

Software or firmware memory 322 can comprise a read only memory (ROM), random access memory (RAM), a miniature hard drive, a flash memory card, or any kind of device (or devices) configured to read instructions from a machine-readable medium or media. The instructions contained in software or firmware memory 322 further include instructions to produce a medical image of suitable resolution for display on the display 340 and/or to send acquired raw or scan converted image data stored in the data memory 330 to an external device (not shown), such as a computer. The image data may be sent from the processor 320 to external device via a wired or wireless network (or direct connection, for example, via a serial or parallel cable or USB port) under control of the processor 320 and a user interface (not shown). In some embodiments, the external device may be a computer or a workstation having a display and memory. The user interface (which may also include the display 340) also receives image data from a user and supplies the data to the processor 320. In some embodiments, the display 340 may include an x-y input, such as a touch-sensitive surface and a stylus (not shown), to facilitate user input.

In an embodiment, a medical imaging system may be configured as a miniaturized device. As used herein, "miniaturized" means that the medical imaging system is a handheld or hand-carried device or configured to be carried in a person's hand, briefcase-sized case, or backpack. For example, a medical imaging system may be a hand-carried device having a size of a typical laptop computer. In an example, the medical imaging system may be an ultrasound imaging system.

Embodiments of the present invention can comprise software or firmware instructing a computer to perform certain actions. Some embodiments of the present invention comprise stand-alone workstation computers that include memory, a display, and a processor. The workstation may also include a user input interface (which may include, for example, a mouse, a touch screen and stylus, a keyboard with cursor keys, or combinations thereof). The memory may include, for example, random access memory (RAM), flash memory, or read-only memory. For purposes of simplicity, devices that can read and/or write media on which computer programs are recorded are also included within the scope of the term "memory." A non-exhaustive list of media that can be read with such a suitable device includes CDs, CD-RWs, DVDs of all types, magnetic media (including floppy disks, tape, and hard drives), flash memory in the form of sticks, cards, and other forms, ROMs, etc., and combinations thereof.

Some embodiments of the present invention may be incorporated into a system, such as an ultrasound imaging system 300 of FIG. 3. In correspondence with a stand-alone workstation, the "computer" can be considered as the apparatus itself, or at least a portion of the components therein. For example, the processor 320 may comprise a general purpose processor with memory, or a separate processor and/or memory may be provided. Display 340 may correspond to the display of the workstation, while the user interface may correspond to the user interface of the workstation. Whether a stand-alone workstation or an imaging apparatus is used, software and/or firmware (hereinafter referred to generically as "software") can be used to instruct the computer to perform the inventive combination of actions described herein. Portions of the software may have specific functions, and these portions are herein referred to as "modules" or "software modules." However, in some embodiments, these modules may comprise one or more electronic hardware components or special-purpose hardware components that may be configured to perform the same purpose as the software module or to aid in the performance of the software module. Thus, a "module" may also refer to hardware or a combination of hardware and software performing a function.

In some embodiments of the present invention, the processor 320 includes a module (not shown) to identify at least one segment in a volumetric image of an object. Alternately, the system 300 may be configured to identify the segment. The segment may be identified manually or automatically. The processor 320 further includes modules that may be implemented within the processor or computer by a stored program and/or within special purpose hardware. These modules include a tracking module 324 configured to track the segment in image data to produce a displacement field. Also, included is an analysis module 326 configured to identify the local deformation of the segment. The analysis module 326 is configured to receive the displacement field from the tracking module 324 and the local deformation is derived from the displacement field. A rendering module 328 is provided in association with the analysis module 326 and is configured to render the 4D representation of the segment with the local deformation. The display 340 is configured to display the enhanced surface or volume rendering. The tracking module 324, the analysis module 326, and the rendering module 328 are configured to operate iteratively to thereby produce an enhanced rendering representing local deformation of the segment. The different modules referred to shall be explained in detail with reference to FIG. 4.

Figure 4:
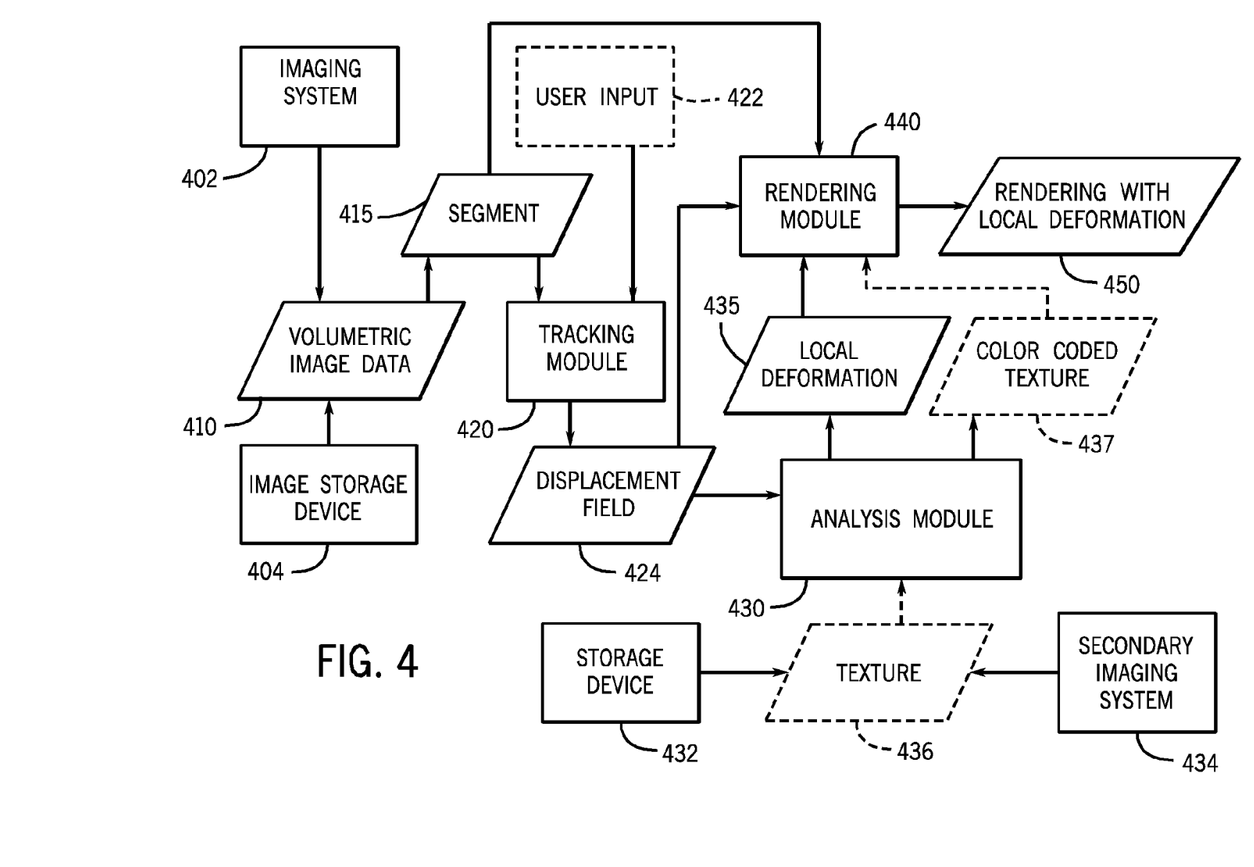
FIG. 4 is a block diagram of a processor assisting in displaying visually enhanced display of motion in a 4D presentation of an object as described in an embodiment of the invention.

FIG. 4 is block diagram of a processor assisting in displaying visually enhanced display of motion in a 4D presentation of an object as described in an embodiment of the invention. Volumetric image data 410 is obtained from an imaging system 402 or from an image storage device 404. From the volumetric image data 410, a segment 415 is defined. The segment 415 may be defined manually or automatically. User input 422 and the segment 415 are provided to a tracking module 420, which tracks the segment 415 to determine a displacement field 424. The user input 422 is not necessarily required for all embodiments of the present invention, and some embodiments need not provide any functionality for gathering user input 422, optionally or otherwise. The user input 422, when provided, includes initialization data, and could include other instructions stored in a software memory such as 322 (see FIG. 3). The tracking module 420 can utilize any known method that can be used to track an object in the segment 415 and produce a displacement field 424. Alternately, the tracking module 420 may track a defined region of interest or the volumetric image data 410 to obtain the displacement field 424. In an embodiment, the object may be a heart and the segment may be a region of the left or right ventricular walls.

The displacement field 424 is provided to an analysis module 430. The analysis module 430 extracts at least the local deformation 435 of the segment 415 from the displacement field 424.

In an embodiment, the analysis module 430 may also be configured to extract at least one quantitative regional parameter representing the motion of the segment 415. The analysis module 430 is optionally provided with a texture 436. The texture 436 could be provided from a storage device 432 or a secondary imaging system 434. The analysis module 430 is further configured to convert the identified quantitative regional parameters into color codes and the color codes may be superimposed onto the texture 436. The color-coded texture 437 representing the quantitative parameters are generated by the analysis module.

The segment 415, along with the displacement field 424 and local deformation 435, is provided to a rendering module 440. The rendering module 440 may be further provided with the color-coded texture 437. Alternately, the color-coded texture 437 may be superimposed on to a surface identified from the volumetric image data 410, and the surface superimposed with the color coded texture 437 may be fed to the rendering module 440 along with the displacement field 424 and local deformation 435. The volumetric image data 410 may also be provided from the imaging system 402 or from the image-storage device 404. The volumetric image data 410, as used herein, may comprise any one or more of image data, synthetic image data, a secondary (or tertiary, etc.) modality of image data (for example, a CT or MRI image), and a cardiac model, or any other volumetric anatomical model. The volumetric image data 410, along with the displacement field 424, the local deformation 435, and the color coded texture 437 is rendered by the rendering module 440 and an enhanced rendering 450 displaying local deformation with at least one regional quantitative parameter superimposed on a texture as the color code is produced.

It should be noted that configurations of the present invention are not limited to cardiac applications or medical applications, in which case the volumetric image data 410 to be displayed would be data representative of a different object having different displacement characteristics.

Figure 5:
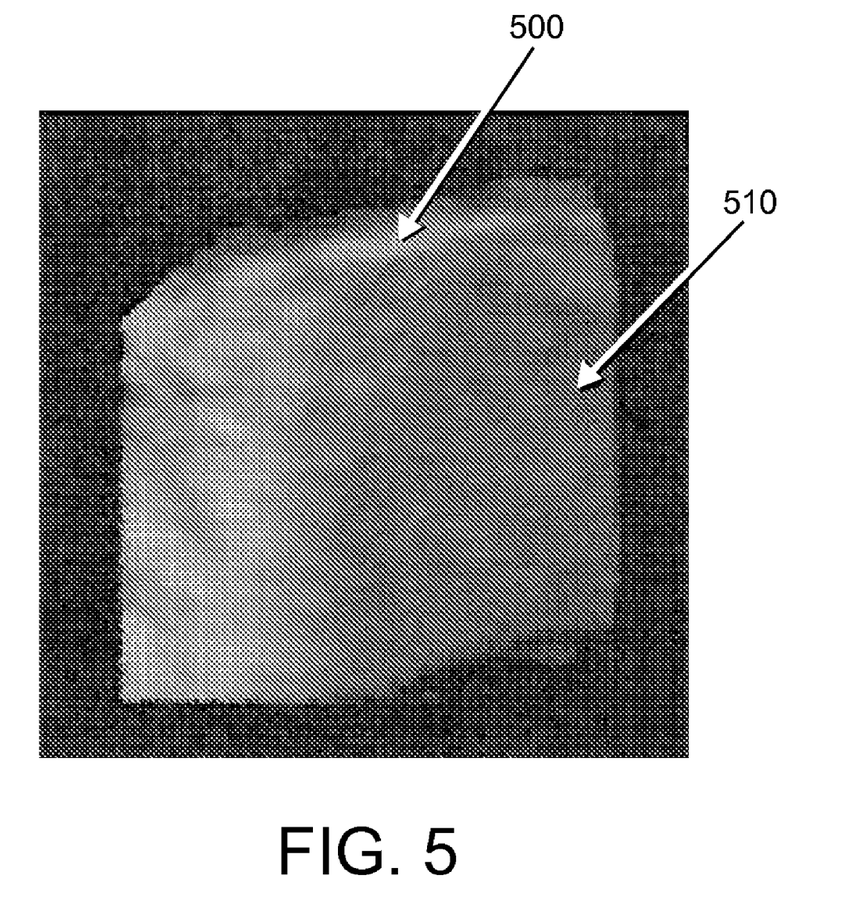
FIG. 5 illustrates volume rendering of a single segment of a left ventricle, displayed in accordance with an embodiment of the invention.

FIG. 5 illustrates volume rendering of a single segment 500 of the left ventricle, displayed in accordance with an embodiment of the invention. In this example, the volume rendering is generated from original 4D data, where the segment boundaries are used as dynamic cropping surfaces. The segment 500 is displayed with color codes 510, shown as different shadings of Red color, representing the quantitative regional parameters. In an example, the regional quantitative parameters may include longitudinal, circumferential, or radial strains.

Figure 6A:
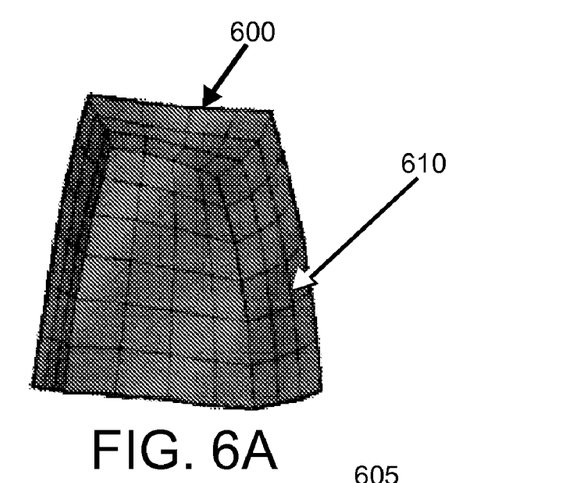
FIGS. 6A to 6C respectively illustrate a surface rendering of a single segment, illustrating ordinary shaded surface rendering with a wire frame, surface rendering with photo-realistic textures of trabeculae, and surface rendering of an artificial speckle pattern.
Figure 6B:
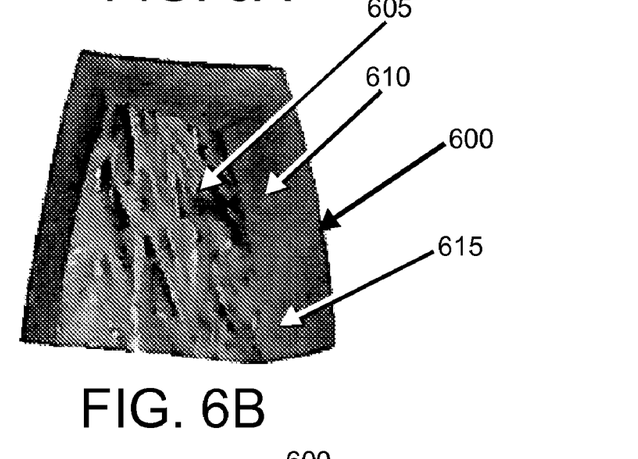
Figure 6C:
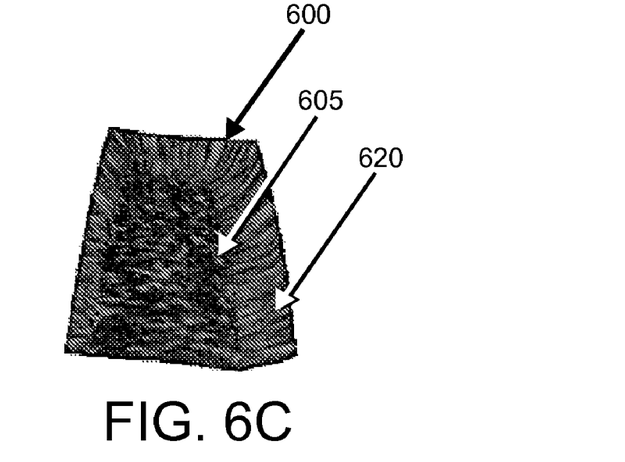

FIGS. 6A to 6C respectively illustrate a surface rendering of a single segment, illustrating ordinary shaded surface rendering with a wire frame, surface rendering with photo-realistic textures of trabeculae, and a surface rendering of an artificial speckle pattern. More specifically, FIG. 6A illustrates surface rendering of a single segment 600 using a wireframe model. The segment 600 is displayed with color codes 610, represented in Red color. FIG. 6B illustrates a surface rendering with color coded texture superimposed on the segment 600. The trabeculae or inner wall of a segment 605 is displayed with a texture 615 superimposed on it. The texture 615 is color coded 610, represented by a different shade of Red color. The color codes 610 represent the quantitative regional parameters. By superimposing the texture 615 onto the surface rendering inner wall of the segment 605, a realistic view is generated. The texture 615 may include artificial endocardial, epicardial, or myocardial like pattern. FIG. 6C illustrates a surface rendering with an artificial speckle pattern on the segment 600. The trabeculae 605 or inner wall of the segment 600 is displayed with an artificial speckle pattern 620.

Figure 7A:
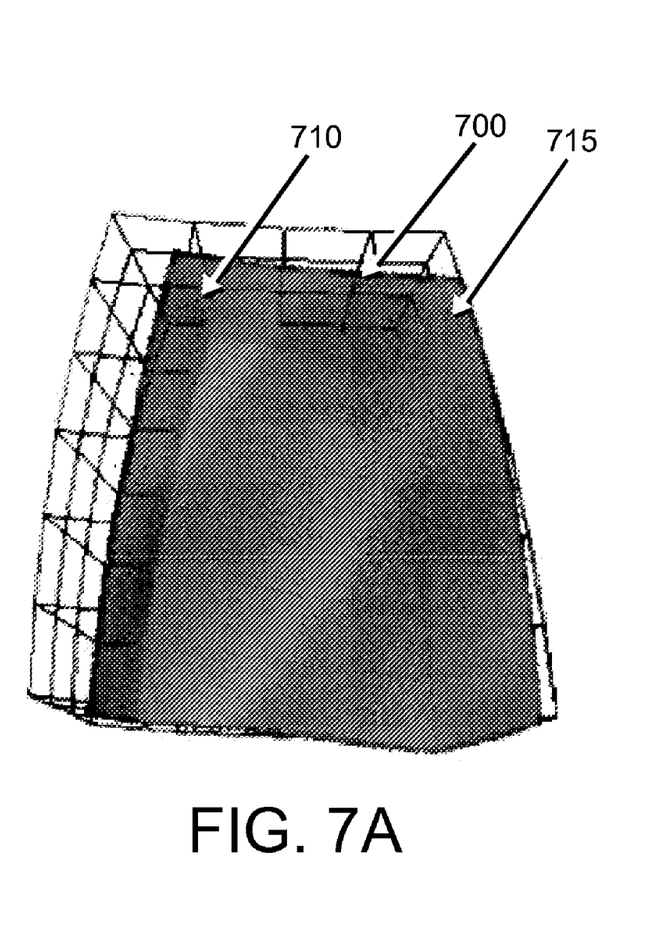
FIGS. 7A and 7B respectively illustrate deformation of a segment through a surface rendering of a single segment using static wireframe mesh and a static semi-transparent model.
Figure 7B:
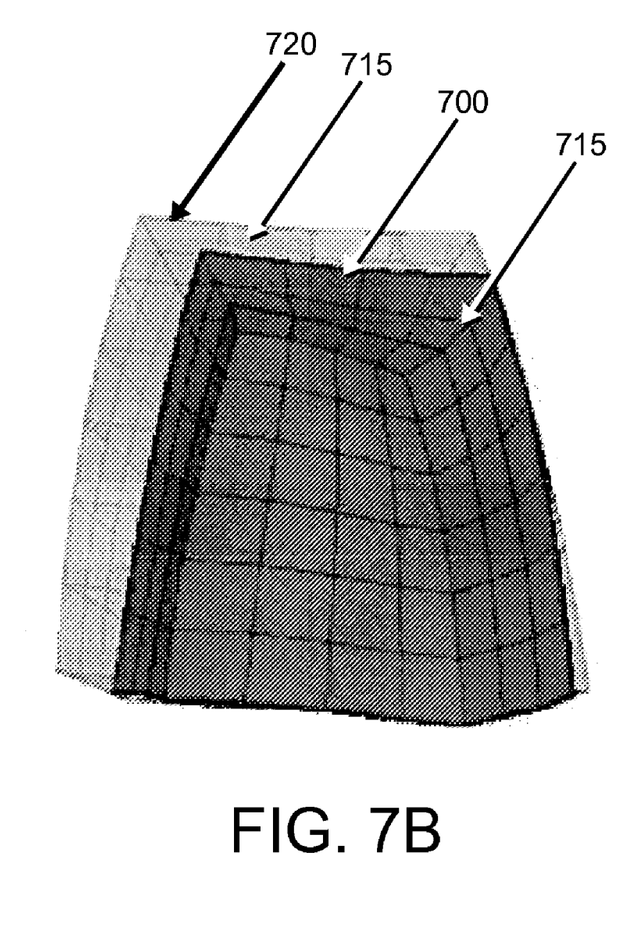

FIGS. 7A and 7B respectively illustrate deformation of a segment using a static wireframe model and a static semi-transparent model. More specifically, FIG. 7A illustrates a segment 700 in a deformed condition rendered with reference to a wireframe model 710. The wireframe model 710 is used to represent the un-deformed segment. Color codes 715 representing quantitative regional parameters are superimposed on the deformed segment 700. Similarly, FIG. 7B illustrates the deformed segment 700 in a deformed condition rendered with reference to a semi transparent wireframe model 720. Color codes 715 representing quantitative regional parameters are superimposed on the deformed segment 700. This display of the deformed segments 700 along with the un-deformed segments using various models gives facilitates easy comparison. Color codes 715 used in the deformed segment 700 and the un-deformed segment 720 on the semi transparent wireframe model are represented with different shades of red. Darker shading is used for the deformed segment 700 compared to the un-deformed model 720.

Figure 8A:
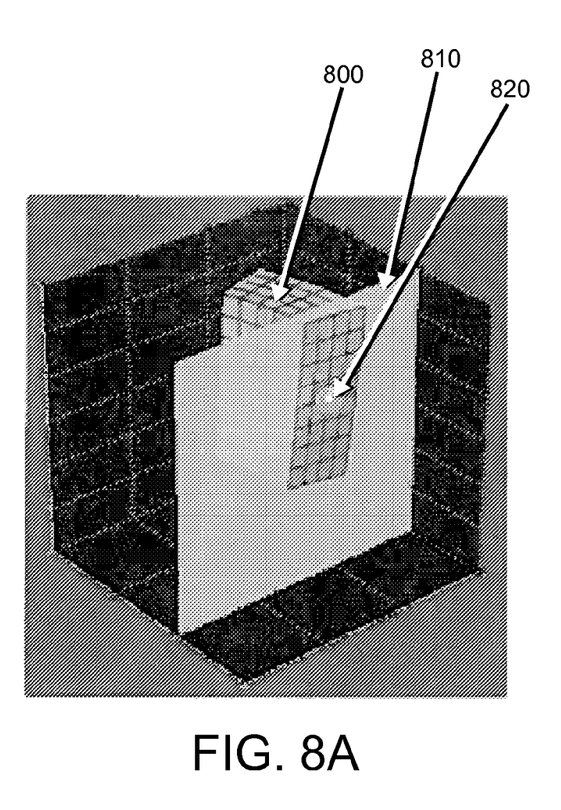
FIGS. 8A and 8B respectively illustrate a segment displayed at two different stages of a cardiac cycle, highlighting the overall motion of the segment.
Figure 8B:
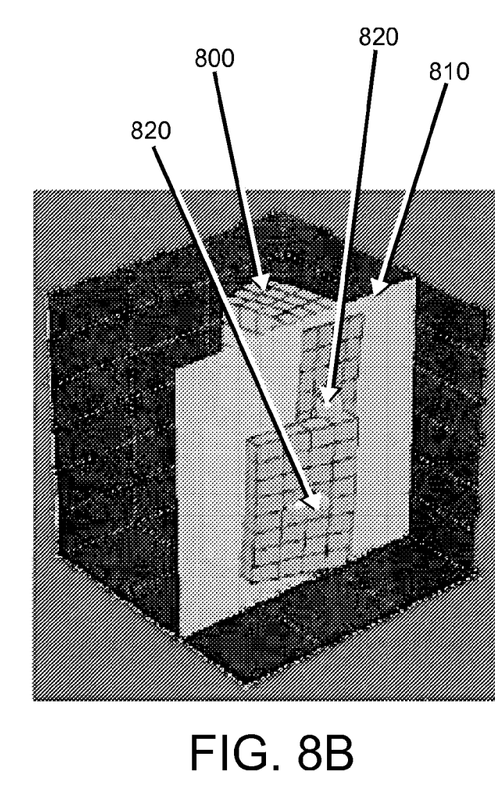

FIGS. 8A and 8B respectively illustrate a segment 800 displayed at two different stages of a cardiac cycle, highlighting overall motion of the segments. More specifically, the segments 800 are displayed at two different stages of the cardiac cycle, for example, at end diastole and end systole, respectively. A static structure, such as a semi-transparent plane 810 is provided to highlight overall motion of the segment 800. Rotation effects are apparent via the semi transparent plane 810. A deformation marker 820 is provided at the face of the segment 800 and indicates principal strains on the segment 800. It is to be noted that at the end of the diastole, the deformation marker 820 is less stretched compared to the end of systole, shown respectively by FIGS. 8A and 8B.

In an embodiment (not shown), the deformation marker 820 is a strain marker and can be color coded based on quantitative parameters. For example, the color coding may represent a ratio between longitudinal and radial strains.

Figure 9A:
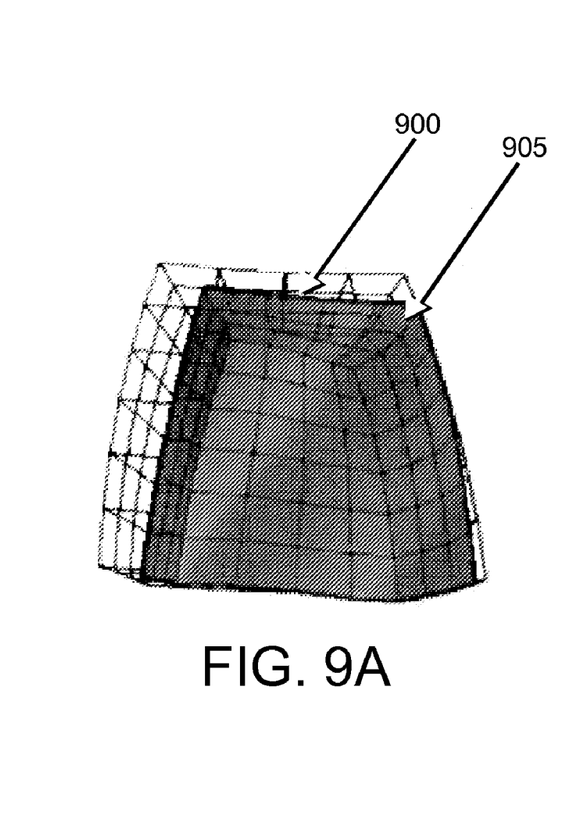
FIGS. 9A and 9B respectively illustrate display of a healthy segment and an infracted segment.
Figure 9B:
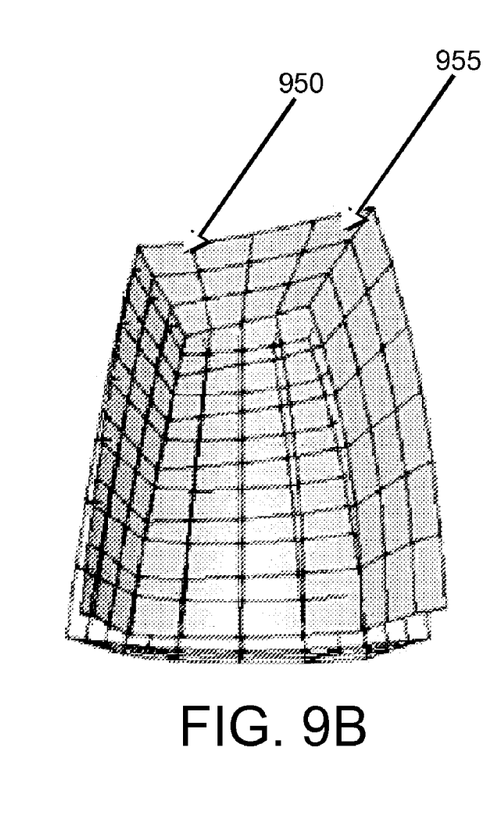

FIGS. 9A and 9B respectively illustrate a surface rendering with a healthy segment and an infracted segment. The healthy segment 900 is displayed in FIG. 9A and the infracted segment 950 is shown in FIG. 9B. The segments are color-coded by quantitative information from the deformation analysis. The healthy segment 900 is shown in red 905 and red denotes contraction. FIG. 9B shows the infracted segment 950 in an expanded position, as shown by blue color 955. The colors convey the regional parameter strain. In an embodiment, a marker (not shown) may be provided to represent the regional parameters.

The various embodiments of the invention provide, volume rendering and surface renderings of single cardiac segments with enhanced visual perception of local deformations. Further more, some of the embodiments provide mappings of quantitative regional parameters on segmental volume or surface renderings.

In yet other embodiments of the present invention, a machine readable medium or media may include, but not limited to, magnetic disks and diskettes, optical disks and diskettes, and/or ROM, flash ROM, and/or battery backed RAM, or any other suitable magnetic, optical, or electronic medium or media). The medium (or media) has recorded thereon instructions configured to instruct a system 300 that includes a computer or processor 320, memory 322, 330, and a display 340, as shown in FIG. 3. The instructions include instructions for tracking an identified segment of a volumetric moving image data to produce a displacement field. The instructions further include instructions identify local deformation of the segment from the displacement field and render the segment based on the displacement field showing the local deformation. The instructions further include instructions to repeat the above-mentioned steps a plurality of times. The repeated steps may further include instructions for identifying quantitative regional parameters from displacement of the three-dimensional data. The repetition thus produces a 4D surface rendered image with texture having color codes representing at least one quantitative regional parameter, displayed along with the local deformation of the segment.

It will thus be appreciated that embodiments of the present invention provide an intuitive display of local deformation in a segmental volume or surface rendering. Embodiments of the present invention are particularly useful in analyzing a cardiac structure in detail.

It is to be understood that the above description is intended to be illustrative and not restrictive. For example, the above-described embodiments (and/or aspects thereof) may be used in combination with each other. In addition, many modifications may be made to adapt a particular situation or material to the teachings of the invention without departing from its scope. While any dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of displaying quantitative segmental data in a four-dimensional presentation of an object, comprising:
   identifying a segment in a volumetric image data;
   repeating the following steps a plurality of times:
     tracking the segment of the volumetric image data to produce a displacement field;
     identifying local deformation of the segment based on the displacement field; and rendering the segment with reference to the displacement field to show the local deformation.

2. The method as claimed in claim 1, wherein the step of identifying the segment comprises: defining the segment manually or automatically.

3. The method as claimed in claim 1, wherein the volumetric image data includes at least one of: ultrasound image data, magnetic resonance image data, or computed tomographic image data.

4. The method as claimed in claim 1, wherein the step of tracking comprises: identifying the displacement field representing motion of the segment.

5. The method as claimed in claim 1, further comprising: identifying at least one regional quantitative parameter.

6. The method as claimed in claim 5, wherein the method further comprises: superimposing the regional quantitative parameters into the segment using a marker or color codes.

7. The method as claimed in claim 5, wherein the regional quantitative parameters include at least one of: stress, strain, velocity, or displacement.

8. The method as claimed in claim 1, wherein the step of rendering comprises: surface rendering the segment with reference to the displacement field.

9. The method as claimed in claim 8, wherein surface rendering of the segment is generated using at least one of: wire frame models, artificial textured models or semi-transparent textured models.

10. The method as claimed in claim 9, wherein a static wire frame model or static semi-transparent model from a reference time is displayed together with a dynamic surface model of the segment.

11. The method as claimed in claim 1, wherein the step of rendering comprises: volume rendering the segment with reference to the displacement field.

12. The method as claimed in claim 11, wherein the volume rendering of a static segment imaged by a template imaging system is performed with reference to the displacement field obtained by a first imaging system.

13. The method as claimed in claim 11, wherein the volume rendering of the segment is generated by applying dynamic cropping surfaces.

14. The method as claimed in claim 1, wherein a plurality of segments is displayed next to each other for visual comparison.

15. The method as claimed in claim 1, further comprising calculating the local deformation from an overall motion of the segment.

16. The method as claimed in claim 15, wherein the overall motion of the segment represents motion of the segment caused by the local deformation and motion caused by at least one other segment in a region of interest.

17. The method as claimed in claim 15, further comprising subtracting the overall motion of the segment from an average motion of the segment to identify the local deformation of the segment.

18. The method as claims in claim 17, further comprising averaging the motion of all points in the segment to obtain the average motion of the segment.

19. A system comprising a computer or processor, memory, and a display, said system configured to: identify a segment of an object in volumetric image data; said system further including:
a tracking module configured to track the segment to produce a displacement field;
an analysis module configured to identify local deformation of the segment from the displacement field; and
a rendering module configured to render the segment with reference to the displacement field to show the local deformation;
wherein the tracking module, analysis module and rendering module are configured to operate iteratively to thereby produce a visually enhanced segmental deformation display in a four-dimensional presentation.

20. The system as claimed in claim 19, wherein the analysis module is further configured to identify at least one regional quantitative parameter with reference to the displacement field and superimpose the same as color codes onto the segment.

21. The system as claimed in claim 19, wherein the system is an ultrasound imaging system further comprising an ultrasound probe, the system is configured to obtain 4D image data using the ultrasound probe, and the 4D image data is ultrasound image data.

22. A non-transitory machine readable medium or media having recorded thereon instructions configured to instruct a system comprising a computer or processor, memory, and a display, comprising:
a routine for obtaining a displacement field representing motion of a segment;
a routine for identifying local deformation of the segment from the displacement field; and
a routine for rendering the segment with reference to the displacement field thereby displaying the local deformation.

* * * * *